United States Patent
Butler et al.

(10) Patent No.: US 9,556,084 B2
(45) Date of Patent: Jan. 31, 2017

(54) PROCESS FOR THE REDUCTION OF ALKYLATION CATALYST DEACTIVATION UTILIZING LOW SILICA TO ALUMINA RATIO CATALYST

(71) Applicant: FINA TECHNOLOGY, INC., Houston, TX (US)

(72) Inventors: James R. Butler, Spicewood, TX (US); Xin Xiao, Augusta, GA (US); James T. Merrill, Morgan, TX (US)

(73) Assignee: FINA TECHNOLOGY, INC., Houston, TX (US)

(*) Notice: Subject to any disclaimer, the term of this patent is extended or adjusted under 35 U.S.C. 154(b) by 11 days.

(21) Appl. No.: 14/154,422

(22) Filed: Jan. 14, 2014

(65) Prior Publication Data
US 2014/0128651 A1    May 8, 2014

Related U.S. Application Data

(63) Continuation of application No. 14/014,098, filed on Aug. 29, 2013, now Pat. No. 8,680,354, which is a continuation of application No. 13/863,722, filed on Apr. 16, 2013, now Pat. No. 8,552,238, which is a continuation of application No. 13/212,234, filed on
(Continued)

(51) Int. Cl.
| | |
|---|---|
| *C07C 2/66* | (2006.01) |
| *B01J 29/06* | (2006.01) |
| *B01J 29/70* | (2006.01) |
| *C07C 6/12* | (2006.01) |
| *C07C 7/12* | (2006.01) |
| *C07C 15/073* | (2006.01) |

(52) U.S. Cl.
CPC .............. *C07C 2/66* (2013.01); *B01J 29/06* (2013.01); *B01J 29/7057* (2013.01); *C07C 6/126* (2013.01); *C07C 7/12* (2013.01); *C07C 15/073* (2013.01); *B01J 2219/00006* (2013.01); *C07C 2529/08* (2013.01); *C07C 2529/70* (2013.01); *Y02P 20/52* (2015.11); *Y02P 20/584* (2015.11); *Y02P 20/588* (2015.11)

(58) Field of Classification Search
CPC ........................................................ C07C 2/66
USPC ................................... 585/449, 448, 467
See application file for complete search history.

(56) References Cited

U.S. PATENT DOCUMENTS

| | | |
|---|---|---|
| 3,308,069 A | 3/1967 | Wadlinger et al. |
| 4,185,040 A | 1/1980 | Ward et al. |

(Continued)

FOREIGN PATENT DOCUMENTS

| | | |
|---|---|---|
| WO | 9429245 | 12/1994 |

*Primary Examiner* — Thuan D Dang
(74) *Attorney, Agent, or Firm* — Albert Shung

(57) ABSTRACT

Alkylation systems and methods of minimizing alkylation catalyst regeneration are described herein. The alkylation systems generally include a preliminary alkylation system adapted to receive an input stream including an alkyl aromatic hydrocarbon and contact the input stream with a preliminary alkylation catalyst disposed therein to form a first output stream. The preliminary alkylation catalyst generally includes a zeolite catalyst having a $SiO_2/Al_2O_3$ ratio of less than about 25. The alkylation systems further include a first alkylation system adapted to receive the first output stream and contact the first output stream with a first alkylation catalyst disposed therein and an alkylating agent to form a second output stream.

22 Claims, 2 Drawing Sheets

Related U.S. Application Data

Aug. 18, 2011, which is a continuation of application No. 11/515,679, filed on Sep. 5, 2006, now abandoned.

(56) References Cited

U.S. PATENT DOCUMENTS

| | | | |
|---|---|---|---|
| 4,642,226 A | | 2/1987 | Calvert et al. |
| 4,992,606 A | | 2/1991 | Kushnerick et al. |
| 5,258,565 A | | 11/1993 | Kresge et al. |
| 5,334,795 A | * | 8/1994 | Chu .......................... C07C 2/66 585/446 |
| 5,453,554 A | | 9/1995 | Cheng et al. |
| 6,297,417 B1 | * | 10/2001 | Samson .................... C07C 2/66 585/448 |
| 7,501,547 B2 | * | 3/2009 | Clark et al. ................... 585/449 |
| 2003/0149324 A1 | * | 8/2003 | Venkat ....................... C07C 7/13 585/820 |

* cited by examiner

PROCESS FOR THE REDUCTION OF ALKYLATION CATALYST DEACTIVATION UTILIZING LOW SILICA TO ALUMINA RATIO CATALYST

CROSS-REFERENCE TO RELATED APPLICATIONS

This application is a continuation application of U.S. application Ser. No. 14/014,098, filed on Aug. 29, 2013, which is a continuation application of U.S. application Ser. No. 13/863,722, filed on Apr. 16, 2013, now issued as U.S. Pat. No. 8,552,238, which is a continuation application of U.S. application Ser. No. 13/212,234, filed on Aug. 18, 2011, which is a continuation of U.S. application Ser. No. 11/515,679, filed on Sep. 5, 2006, now abandoned.

FIELD

Embodiments of the present invention generally relate to alkylation of aromatic compounds. In particular, embodiments of the invention generally relate to reducing the deactivation of the alkylation catalyst within alkylation systems.

BACKGROUND

Alkylation reactions generally involve contacting a first aromatic compound with an alkylation catalyst to form a second aromatic compound. Unfortunately, alkylation catalysts generally experience deactivation requiring either regeneration or replacement. Some of the deactivation results from poisons present in the input stream to the alkylation system. Therefore, a need exists to develop an alkylation system that is capable of reducing alkylation catalyst deactivation.

SUMMARY

Embodiments of the present invention include alkylation systems. The alkylation systems generally include a preliminary alkylation system adapted to receive an input stream including an alkyl aromatic hydrocarbon and contact the input stream with a preliminary alkylation catalyst disposed therein to form a first output stream. The preliminary alkylation catalyst generally includes a zeolite catalyst having a $SiO_2/Al_2O_3$ ratio of less than about 25. The alkylation systems may further include a first alkylation system adapted to receive the first output stream and contact the first output stream with a first alkylation catalyst disposed therein and an alkylating agent to form a second output stream.

In one embodiment, the alkylation system includes a preliminary alkylation catalyst having a first $SiO_2/Al_2O_3$ ratio and a first alkylation catalyst having a second $SiO_2/Al_2O_3$ ratio, wherein the first $SiO_2/Al_2O_3$ ratio is lower than the second $SiO_2/Al_2O_3$ ratio.

Embodiments further include methods of minimizing alkylation catalyst regeneration. Such methods generally include substantially continuously introducing an alkyl aromatic hydrocarbon and an alkylating agent to an alkylation system having an alkylation catalyst disposed therein, contacting the input stream with the alkylation catalyst to form an output stream and withdrawing the output stream from the alkylation system over a period of time substantially equal to a life of the alkylation catalyst. The methods further include contacting the input stream with a preliminary catalyst including a zeolite catalyst having a $SiO_2/Al_2O_3$ ratio of 25 or less prior to feeding the input stream to the alkylation system. Such methods generally result in an alkylation catalyst life that is longer than the same alkylation catalyst's life in the absence of contact with the preliminary catalyst.

DETAILED DESCRIPTION

Introduction and Definitions

Figure 1A:
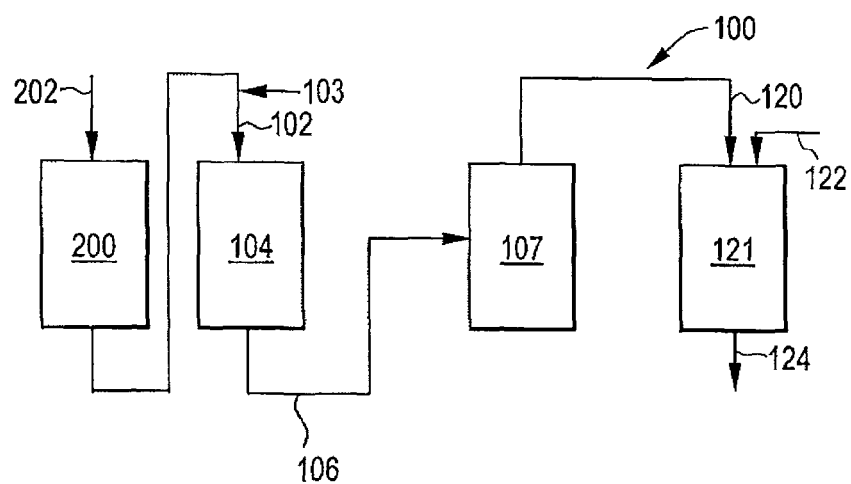
FIG. 1A illustrates an embodiment of an alkylation system.

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions when the information in this patent is combined with available information and technology.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

The term "activity" refers to the weight of product produced per weight of the catalyst used in a process per hour of reaction at a standard set of conditions (e.g., grams product/gram catalyst/hr).

The term "alkylation" refers to the addition of an alkyl group to another molecule.

The term "deactivated catalyst" refers to a catalyst that has lost enough catalyst activity to no longer be efficient in a specified process. Such efficiency is determined by individual process parameters. Further, the time from introduction of the catalyst to a system to the point that the catalyst is a deactivated catalyst is generally referred to as the catalyst life.

The term "processing" is not limiting and includes agitating, mixing, milling, blending and combinations thereof, all of which are used interchangeably herein. Unless otherwise specified, the processing may occur in one or more vessels, such vessels being known to one skilled in the art.

The term "recycle" refers to returning an output of a system as input to either that same system or another system within a process. The output may be recycled to the system in any manner known to one skilled in the art, for example, by combining the output with an input stream or by directly feeding the output into the system. In addition, multiple input/recycle streams may be fed to a system in any manner known to one skilled in the art.

The term "regeneration" refers to a process for renewing catalyst activity and/or making a catalyst reusable after its activity has reached an unacceptable/inefficient level.

Examples of such regeneration may include passing steam over a catalyst bed or burning off carbon residue, for example.

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process. The term "zeolite" refers to a molecular sieve containing a silicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

FIG. 1 illustrates a schematic block diagram of an embodiment of an alkylation/transalkylation process 100. Although not shown herein, the process stream flow may be modified based on unit optimization so long as the modification complies with the spirit of the invention, as defined by the claims. For example, at least a portion of any overhead fraction may be recycled as input to any other system within the process and/or any process stream may be split into multiple process stream inputs, for example. Also, additional process equipment, such as heat exchangers, may be employed in the processes described herein and such use is generally known to one skilled in the art. Further, while described below in terms of primary components, the streams indicated below may include any additional components as known to one skilled in the art.

As shown in FIG. 1A, the process 100 generally includes supplying an input stream 102 (e.g., a first input stream) to an alkylation system 104 (e.g., a first alkylation system). The alkylation system 104 is generally adapted to contact the input stream 102 with an alkylation catalyst to form an alkylation output stream 106 (e.g., a first output stream). In addition to the input stream 102, an additional input, such as an alkylating agent, may be supplied to the alkylation system 104 via line 103.

Figure 1B:
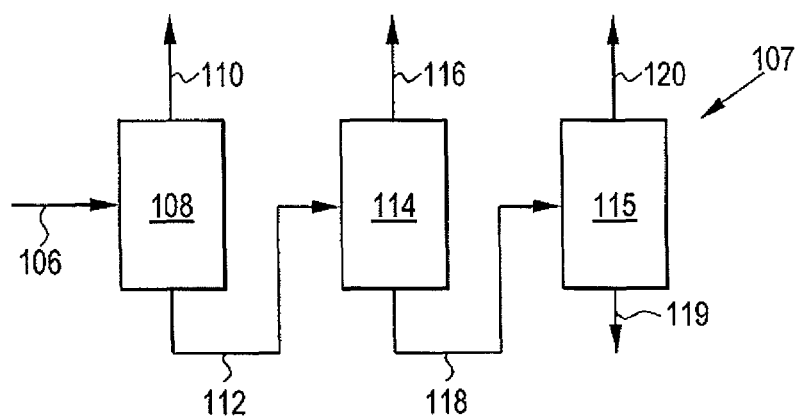
FIG. 1B illustrates an embodiment of a separation system.

At least a portion of the alkylation output stream 106 passes to a separation system 107 (see, FIG. 1B). The separation system 107 generally includes a plurality of vessels, such vessels being adapted to separate components of the output stream 106. As shown in FIG. 1B, at least a portion of the separation system output 120, described in further detail below, is passed from the separation system 107 to a second alkylation system 121 (e.g., a transalkylation system) as transalkylation input 120.

In addition to the transalkylation input 120, an additional input, such as additional aromatic compound, may be supplied to the second alkylation system 121, which may alternatively be referred to as a transalkylation system, via line 122 to contact a transalkyation catalyst disposed therein and form a transalkylation output 124.

The input stream 102 generally includes a first aromatic compound. The aromatic compound may include substituted or unsubstituted aromatic compounds. If present, the substituents on the aromatic compounds may be independently selected from alkyl, aryl, alkaryl, alkoxy, aryloxy, cycloalkyl, halide and/or other groups that do not interfere with the alkylation reaction, for example. Examples of substituted aromatic compounds generally include toluene, xylene, isopropylbenzene, normal propylbenzene, alpha-methylnaphthalene, ethylbenzene, mesitylene, durene, cymene, butylbenzene, pseudocumene, o-diethylbenzene, m-diethylbenzene, p-diethylbenzene, isoamylbenzene, iso-hexylbenzene, pentaethylbenzene, pentamethylbenzene, 1,2,3,4-tetraethylbenzene, 1,2,3,5-tetramethylbenzene, 1,2,4-triethylbenzene, 1,2,3-trimethylbenzene, m-butyltoluene, p-butyltoluene, 3,5-diethyltoluene, o-ethyltoluene, p-ethyltoluene, m-propyltoluene, 4-ethyl-m-xylene, dimethylnaphthalenes, ethylnaphthalene, 2,3-dimethylanthracene, 9-ethylanthracene, 2-methylanthracene, o-methylanthracene, 9,10-dimethylphenanthrene and 3-methyl-phenanthrene. Further examples of aromatic compounds include hexylbenzene, nonylbenzene, dodecylbenzene, pentadecylbenzene, hexyltoluene, nonyltoluene, dodecyltoluene and pentadecyltoluene.

In one embodiment, the aromatic compound includes one or more hydrocarbons, such as benzene, naphthalene, anthracene, naphthacene, perylene, coronene and phenanthrene, for example. In another embodiment, the first aromatic compound includes benzene. The benzene may be supplied from a variety of sources, such as a fresh benzene source and/or a variety of recycle sources, for example. As used herein, the term "fresh benzene source" refers to a source including at least about 95 wt. % benzene, at least about 98 wt. % benzene or at least about 99 wt. % benzene, for example.

The alkylating agent may include olefins (e.g., ethylene, propylene, butene and pentene), alcohols (e.g., methanol, ethanol, propanol, butanol and pentanol), aldehydes (e.g., formaldehyde, acetaldehyde, propionaldehyde, butyraldehyde and n-valeraldehyde) and/or alkyl halides (e.g., methyl chloride, ethyl chloride, propyl chloride, butyl chloride and pentyl chloride), for example. In one embodiment, the alkylating agent includes a mixture of light olefins, such as mixtures of ethylene, propylene, butene and/or pentenes, for example. In another embodiment, the alkylating agent includes ethylene.

In addition to the first aromatic compound and the alkylating agent, the input stream 102 and/or line 103 may further include other compounds in minor amounts (e.g., sometimes referred to as poisons or inactive compounds), such as $C_7$ aliphatic compounds and/or nonaromatic compounds, for example. In one embodiment, the input stream 102 includes less than about 3% of such compounds or less than about 1%, for example (e.g., about 100 ppb or less, or about 80 ppb or less or about 50 ppb or less).

The alkylation system 104 generally includes one or more reaction vessels. The reaction vessels may include continuous flow reactors (e.g., fixed-bed, slurry bed or fluidized bed), for example. In one embodiment, the alkylation system 104 includes a plurality of multi-stage reaction vessels (not shown). For example, the plurality of multi-stage reaction vessels may include a plurality of operably connected catalyst beds, such beds containing an alkylation catalyst (not shown). The number of catalyst beds is generally determined by individual process parameters, but may include from 2 to 20 catalyst beds or from 3 to 10 catalyst beds, for example.

Such reaction vessels may be liquid phase, vapor phase, supercritical phase or mixed phase reactors operated at reactor temperatures and pressures sufficient to maintain the alkylation reaction in the corresponding phase, i.e., the phase of the aromatic compound, for example. Such temperatures and pressures are generally determined by individual process parameters. In one embodiment, the plurality of stages within a reaction vessel may be operated with the same or different catalyst and at the same or different temperatures and space velocities. Such temperatures and pressures are generally determined by individual process parameters. However, liquid phase reactions may occur at temperatures of from about 160° C. to about 270° C. and pressures of from about 400 psig to about 700 psig, for example. Vapor phase reactions may occur at temperatures of from about 350° C. to about 500° C. and pressures of from about 200 psig to about 355 psig, for example.

The alkylation catalyst may include a molecular sieve catalyst. Such molecular sieve catalyst may include zeolite beta, zeolite Y, 25M-5, zeolite MCM-22, zeolite MCM-36, zeolite MCM-49 or zeolite MCM-56, for example. In one embodiment, the catalyst is a zeolite beta having a silica to alumina molar ratio (expressed as $SiO_2/Al_2O_3$ ratio) of from about 5 to about 200 or from about 20 to about 100, for example. In one embodiment, the zeolite beta may have a low sodium content, e.g., less than about 0.2 wt. % expressed as $Na_2O$, or less than about 0.02 wt. %, for example. The sodium content may be reduced by any method known to one skilled in the art, such as through ion exchange, for example. (See, U.S. Pat. No. 3,308,069 and U.S. Pat. No. 4,642,226 (formation of zeolite beta), U.S. Pat. No. 4,185,040 (formation of zeolite Y), U.S. Pat. No. 4,992,606 (formation of MCM-22), U.S. Pat. No. 5,258,565 (formation of MCM-36), WO 94/29245 (formation of MCM-49) and U.S. Pat. No. 5,453,554 (formation of MCM-56), which are incorporated by reference herein.)

In one specific embodiment, the alkylation catalyst includes a rare earth modified catalyst, such as a cerium promoted zeolite catalyst. In one embodiment, the cerium promoted zeolite catalyst is a cerium promoted zeolite beta catalyst. The cerium promoted zeolite beta (e.g., cerium beta) catalyst may be formed from any zeolite catalyst known to one skilled in the art. For example, the cerium beta catalyst may include zeolite beta modified by the inclusion of cerium. Any method of modifying the zeolite beta catalyst with cerium may be used. For example, in one embodiment, the zeolite beta may be formed by mildly agitating a reaction mixture including an alkyl metal halide and an organic templating agent (e.g., a material used to form the zeolite structure) for a time sufficient to crystallize the reaction mixture and form the zeolite beta (e.g., from about 1 day to many months via hydrothermal digestion), for example. The alkyl metal halide may include silica, alumina, sodium or another alkyl metal oxide, for example. The hydrothermal digestion may occur at temperatures of from slightly below the boiling point of water at atmospheric pressure to about 170° C. at pressures equal to or greater than the vapor pressure of water at the temperature involved, for example.

The cerium promoted zeolite beta may have a silica to alumina molar ratio (expressed as $SiO_2/Al_2O_3$ ratio) of from about 10 to about 200 or about 50 to 100, for example.

The alkylation catalyst may optionally be bound to, supported on or extruded with any support material. For example, the alkylation catalyst may be bound to a support to increase the catalyst strength and attrition resistance to degradation. The support material may include alumina, silica, aluminosilicate, titanium and/or clay, for example.

The alkylation output 106 generally includes a second aromatic compound formed from the reaction of the first aromatic compound and the alkylating agent in the presence of the alkylation catalyst, for example. In a specific embodiment, the second aromatic compound includes ethylbenzene.

The transalkylation system 121 generally includes one or more reaction vessels having a transalkylation catalyst disposed therein. The reaction vessels may include any reaction vessel, combination of reaction vessels and/or number of reaction vessels (either in parallel or in series) known to one skilled in the art. Such temperatures and pressures are generally determined by individual process parameters. However, liquid phase reactions may occur at temperatures of from about 65° C. to about 290° C. (e.g., the critical temperature of the first aromatic compound) and pressures of from about 800 psig or less, for example. Vapor phase reactions may occur at temperatures of from about 350° C. to about 500° C. and pressures of from about 200 psi to about 500 psi, for example.

The transalkylation output 124 generally includes the second aromatic compound, for example. As stated previously, any of the process streams, such as the transalkylation output 124, may be used for any suitable purpose or recycled back as input to another portion of the system 100, such as the separation system 107, for example.

The transalkylation catalyst may include a molecular sieve catalyst and may be the same catalyst or a different catalyst than the alkylation catalyst, for example. Such molecular sieve catalyst may include zeolite beta, zeolite Y, zeolite MCM-22, zeolite MCM-36, zeolite MCM-49 or zeolite MCM-56, for example.

In a specific embodiment, the first aromatic compound includes benzene and the first alkylating agent includes ethylene. In one embodiment, the molar ratio of benzene to ethylene entering the alkylation system 104 may be from about 1:1 to about 30:1, or from about 1:1 to about 20:1 or from about 5:1 to about 15:1 and the space velocity may be from about 2 to about 10, for example.

In a specific embodiment, the separation system (or product recovery) 107 includes three separation zones (illustrated in FIG. 1B) operated at conditions known to one skilled in the art. The first separation zone 108 may include any process or combination of processes known to one skilled in the art for the separation of aromatic compounds. For example, the first separation zone 108 may include one or more distillation columns (not shown), either in series or in parallel. The number of such columns may depend on the volume of the alkylation output 106 passing therethrough, for example.

The overhead fraction 110 from the first column 108 generally includes the first aromatic compound, such as benzene, for example. The bottoms fraction 112 from the first separation zone 108 generally includes the second aromatic compound, such as ethylbenzene, for example. The bottoms fraction 112 further includes additional components, which may undergo further separation in the second separation zone 114 and third separation zone 115, discussed further below.

The second separation zone 114 may include any process known to one skilled in the art, for example, one or more distillation columns (not shown), either in series or in parallel. The overhead fraction 116 from the second separation zone 114 generally includes the second aromatic compound, such as ethylbenzene, which may be recovered and used for any suitable purpose, such as the production of styrene, for example. The bottoms fraction 118 from the second separation zone 114 generally includes heavier aromatic compounds, such as polyethylbenzene, cumene and/or butylbenzene, for example, which may undergo further separation in the third separation zone 115.

The third separation zone 115 generally includes any process known to one skilled in the art, for example, one or more distillation columns (not shown), either in series or in parallel. In a specific embodiment, the overhead fraction 120 from the third separation zone 115 may include diethylbenzene and liquid phase triethylbenzene, for example. The bottoms fraction 119 (e.g., heavies) may be recovered from the third separation zone 115 for further processing and recovery (not shown).

Unfortunately, alkylation and transalkylation catalysts generally experience deactivation upon exposure to reaction. The deactivation results from a number of factors. One of those factors is that poisons present in the input stream 102, such as nitrogen, sulfur and/or oxygen containing impurities, either naturally occurring or a result of a prior process, may reduce the activity of the alkylation catalyst.

Therefore, the alkylation/transalkylation system 100 further includes a preliminary alkylation system 200. The preliminary alkylation input stream 202 may be passed through the preliminary alkylation system 200 prior to entry into the alkylation system 104 to reduce the level of poisons in the input stream 102, for example. In one embodiment, the level of poisons is reduced by at least 10%, or at least 20% or at least 30% or at least 40% or at least 50%, for example.

The preliminary alkylation system 200 may be maintained at ambient or up to alkylation conditions, for example. For example, the preliminary alkylation system 200 may be operated under liquid phase and/or vapor phase conditions. For example, the preliminary alkylation system 200 may be operated at a temperature of from about 20° C. to about 270° C. and a pressure of from about 675 kPa to about 8300 kPa.

The preliminary alkylation system 200 generally includes a preliminary alkylation catalyst disposed therein. The alkylation catalyst, transalkylation catalyst and/or the preliminary catalyst may be the same or different. In general, such catalysts include molecular sieve catalysts, such as zeolite Y or zeolite beta catalysts, for example.

As a result of the level of poisons present in the preliminary alkylation input 202, the preliminary catalyst in the preliminary alkylation system 200 has typically deactivated rapidly, requiring frequent regeneration and/or replacement. For example, the preliminary catalyst may experience deactivation more rapidly than the alkylation catalyst (e.g., from about twice as often to about 1.5 times as often). Previous systems have generally used the preliminary alkylation system 200 as a sacrificial system, thereby reducing the amount of poisons contacting the alkylation catalyst in the alkylation system 104.

However, embodiments of the invention utilize a catalyst having a lower $SiO_2/Al_2O_3$ ratio than those preliminary alkylation catalysts previously used (and discussed herein). For example, the preliminary alkylation catalyst may have a $SiO_2/Al_2O_3$ ratio that is about 50 or less, or that is about 25 or less, or that is from about 5 to about 50 or from about 7.5 to about 25, for example.

In one specific, non-limiting embodiment, the preliminary alkylation catalyst has a $SiO_2/Al_2O_3$ ratio that is lower than the $SiO_2/Al_2O_3$ ratio of the alkylation catalyst. For example, the preliminary alkylation catalyst may have a $SiO_2/Al_2O_3$ ratio that is at least about 25%, or at least about 50%, or at least about 75% or at least about 90% lower than the $SiO_2/Al_2O_3$ ratio of the alkylation catalyst.

The preliminary alkylation catalyst may include any commercially available catalyst having the $SiO_2/Al_2O_3$ ratio discussed herein. For example, the preliminary alkylation catalyst may include Y-84 zeolite (i.e., $SiO_2/Al_2O_3$ ratio of 9.1), for example.

Further, while not described in detail herein, it is contemplated that the preliminary alkylation catalyst may include a plurality of preliminary alkylation catalysts so long as at least one of the plurality of preliminary alkylation catalysts include the lower $SiO_2/Al_2O_3$ ratio preliminary alkylation catalyst described herein.

Unexpectedly, it has been found that the embodiments described herein result in significantly reduced, if not eliminated, deactivation of all catalysts within the alkylation system.

However, when regeneration of any catalyst within the system is desired, the regeneration procedure may includes processing the deactivated catalyst at high temperatures, although the regeneration may include any regeneration procedure known to one skilled in the art.

Once a reactor is taken off-line, the catalyst disposed therein may be purged. Off-stream reactor purging may be performed by contacting the catalyst in the off-line reactor with a purging stream, which may include any suitable inert gas (e.g., nitrogen), for example. The off-stream reactor purging conditions are generally determined by individual process parameters and are generally known to one skilled in the art.

The catalyst may then undergo regeneration. The regeneration conditions may be any conditions that are effective for at least partially reactivating the catalyst and are generally known to one skilled in the art. For example, regeneration may include heating the catalyst to a temperature or a series of temperatures, such as a regeneration temperature of from about 50° C. to about 400° C. above the purging or reaction temperature, for example.

In one specific non-limiting embodiment, the alkylation catalyst is heated to a first temperature (e.g., 700° F.) with a gas containing nitrogen and about 2% oxygen, for example, for a time sufficient to provide an output stream having an oxygen content of about 0.5%. The catalyst may then be heated to a second temperature for a time sufficient to provide an output stream having an oxygen content of about 2.0%. The second temperature may be about 50° F. greater than the first temperature, for example. The second temperature is generally about 950° F. or less, for example. The catalyst may further be held at the second temperature for a period of time, or at a third temperature that is greater than the second temperature, for example.

Upon catalyst regeneration, the catalyst may then be reused for alkylation and transalkylation, for example.

While the foregoing is directed to embodiments of the present invention, other and further embodiments of the invention may be devised without departing from the basic scope thereof and the scope thereof is determined by the claims that follow.

What is claimed is:

1. A process for producing an alkylaromatic compound, the process comprising:
    (a) introducing an input stream comprising an aromatic hydrocarbon, and an alkylating agent comprising an alkene into a preliminary alkylation system comprising a preliminary alkylation catalyst having a first $SiO_2/Al_2O_3$ ratio ranging from 7.5 to 25, said preliminary alkylation catalyst is a zeolite beta;
    (b) operating said preliminary alkylation system under alkylation conditions to produce said alkylaromatic compound, said conditions being such that said aromatic hydrocarbon is at least partly in the liquid phase;
    (c) withdrawing from said preliminary alkylation system a first output stream comprising said alkylaromatic compound and unreacted aromatic hydrocarbon and about 100 ppb or less of catalyst poisons, wherein the amount of catalyst poisons in the first output stream is at least 10% less than the amount of catalyst poisons in the input stream, wherein the catalyst poisons are nitrogen containing impurities;

(d) introducing at least part of said first output stream and an alkylating agent into a first alkylation system comprising a first alkylation catalyst having a second SiO2/Al2O3 ratio, said first alkylation catalyst is a molecular sieve; and wherein the preliminary alkylation catalyst and the first alkylation catalyst are different in that the preliminary alkylation catalyst has a SiO2/Al2O3 ratio that is at least 25% lower than the first alkylation catalyst;

(e) operating said first alkylation system under alkylation conditions to produce said alkylaromatic compound, said conditions being such that said aromatic hydrocarbon is at least partly in the liquid phase;

(f) withdrawing from said first alkylation system a second output stream comprising said alkylaromatic compound.

2. The process of claim 1, wherein said alkylating agent includes ethylene, said aromatic hydrocarbon includes benzene and said alkylaromatic compound includes ethylbenzene.

3. The process of claim 1, wherein the preliminary alkylation system is operated at a temperature of from about 20° C. to about 270° C.

4. The process of claim 1, wherein the preliminary alkylation system is operated at a temperature of from about 675 kPs to about 8300 kPa.

5. The process of claim 1, wherein the amount of catalyst poisons in the first output stream is at least 20% less than the amount of catalyst poisons in the input stream.

6. The process of claim 1, wherein the amount of catalyst poisons in the first output stream is at least 30% less than the amount of catalyst poisons in the input stream.

7. The process of claim 1, wherein the amount of catalyst poisons in the first output stream is at least 40% less than the amount of catalyst poisons in the input stream.

8. The process of claim 1, wherein the amount of catalyst poisons in the first output stream is at least 50% less than the amount of catalyst poisons in the input stream.

9. The process of claim 1, wherein the preliminary alkylation catalyst has a $SiO_2/Al_2O_3$ ratio at least 75% lower than the first alkylation catalyst.

10. The process of claim 1, wherein the preliminary alkylation catalyst has a $SiO_2/Al_2O_3$ ratio at least 50% lower than the first alkylation catalyst.

11. The process of claim 1, wherein the preliminary alkylation catalyst has a $SiO_2/Al_2O_3$ ratio at least 90% lower than the first alkylation catalyst.

12. A process for producing an alkylaromatic compound, the process comprising:

(a) introducing an input stream comprising an aromatic hydrocarbon, and an alkylating agent comprising an alkene into a preliminary alkylation system comprising a preliminary alkylation catalyst having a first $SiO_2/Al_2O_3$ ratio ranging from 7.5 to 25, said preliminary alkylation catalyst is a zeolite beta;

(b) operating said preliminary alkylation system under alkylation conditions to produce said alkylaromatic compound, said conditions being such that said aromatic hydrocarbon is at least partly in the liquid phase;

(c) withdrawing from said preliminary alkylation system a first output stream comprising said alkylaromatic compound and unreacted aromatic hydrocarbon; wherein the amount of catalyst poisons in the first output stream is less than the amount of catalyst poisons in the input stream, wherein the catalyst poisons are nitrogen containing impuritites;

(d) introducing at least part of said first output stream and an alkylating agent into a first alkylation system comprising a first alkylation catalyst having a second $SiO_2/Al_2O_3$ ratio, said first alkylation catalyst is a molecular sieve; and wherein the preliminary alkylation catalyst and the first alkylation catalyst are different in that the preliminary alkylation catalyst has a has a $SiO_2/Al_2O_3$ ratio at least 25% lower than the first alkylation catalyst;

(e) operating said first alkylation system under alkylation conditions to produce said alkylaromatic compound, said conditions being such that said aromatic hydrocarbon is at least partly in the liquid phase;

(f) withdrawing from said first alkylation system a second output stream comprising said alkylaromatic compound.

13. The process of claim 12, wherein the preliminary alkylation catalyst has a $SiO_2/Al_2O_3$ ratio at least 50% lower than the first alkylation catalyst.

14. The process of claim 13, wherein the preliminary alkylation catalyst has a $SiO_2/Al_2O_3$ ratio at least 90% lower than the first alkylation catalyst.

15. The process of claim 12, wherein said alkylating agent includes ethylene, said aromatic hydrocarbon includes benzene and said alkylaromatic compound includes ethylbenzene.

16. The process of claim 12, wherein the preliminary alkylation system is operated at a temperature of from about 20° C. to about 270° C.

17. The process of claim 12, wherein the preliminary alkylation system is operated at a temperature of from about 675 kPs to about 8300 kPa.

18. The process of claim 12, wherein the amount of catalyst poisons in the first output stream is at least 10% less than the amount of catalyst poisons in the input stream.

19. The process of claim 12, wherein the amount of catalyst poisons in the first output stream is at least 20% less than the amount of catalyst poisons in the input stream.

20. The process of claim 12, wherein the amount of catalyst poisons in the first output stream is at least 30% less than the amount of catalyst poisons in the input stream.

21. The process of claim 12, wherein the amount of catalyst poisons in the first output stream is at least 40% less than the amount of catalyst poisons in the input stream.

22. The process of claim 12, wherein the amount of catalyst poisons in the first output stream is at least 50% less than the amount of catalyst poisons in the input stream.

\* \* \* \* \*